(12) United States Patent
Brown

(10) Patent No.: US 11,477,587 B2
(45) Date of Patent: Oct. 18, 2022

(54) INDIVIDUALIZED OWN VOICE DETECTION IN A HEARING PROSTHESIS

(71) Applicant: Cochlear Limited, Macquarie University (AU)

(72) Inventor: Matthew Brown, South Coogee (AU)

(73) Assignee: Cochlear Limited, Macquarie University (AU)

( * ) Notice: Subject to any disclaimer, the term of this patent is extended or adjusted under 35 U.S.C. 154(b) by 131 days.

(21) Appl. No.: 16/961,536

(22) PCT Filed: Jan. 9, 2019

(86) PCT No.: PCT/IB2019/050164
§ 371 (c)(1),
(2) Date: Jul. 10, 2020

(87) PCT Pub. No.: WO2019/142072
PCT Pub. Date: Jul. 25, 2019

(65) Prior Publication Data
US 2021/0058720 A1    Feb. 25, 2021

Related U.S. Application Data

(60) Provisional application No. 62/617,750, filed on Jan. 16, 2018.

(51) Int. Cl.
*H04R 25/00* (2006.01)
(52) U.S. Cl.
CPC ......... *H04R 25/606* (2013.01); *H04R 25/554* (2013.01); *H04R 2225/41* (2013.01); *H04R 2225/43* (2013.01)

(58) Field of Classification Search
CPC .............. H04R 2225/41; H04R 25/606; H04R 25/554; H04R 2225/43
(Continued)

(56) References Cited

U.S. PATENT DOCUMENTS 7,340,231 B2    3/2008    Behrens
7,738,667 B2    6/2010    Bramslow
(Continued)

FOREIGN PATENT DOCUMENTS

CN    103874002 A    6/2014
CN    105898651 A    8/2016
(Continued)

OTHER PUBLICATIONS

Extended European Search Report in counterpart European Application No. 19741919.5-1122, dated Sep. 14, 2021, 8 pages.
(Continued)

*Primary Examiner* — Phylesha Dabney
(74) *Attorney, Agent, or Firm* — Edell, Shapiro & Finnan, LLC

(57) ABSTRACT

Presented herein are techniques for training a hearing prosthesis to classify/categorize received sound signals as either including a recipient's own voice (i.e., the voice or speech of the recipient of the hearing prosthesis) or external voice (i.e., the voice or speech of one or more persons other than the recipient). The techniques presented herein use the captured voice (speech) of the recipient to train the hearing prosthesis to perform the classification of the sound signals as including the recipient's own voice or external voice.

32 Claims, 14 Drawing Sheets

(58) Field of Classification Search
USPC .......................................................... 381/314
See application file for complete search history.

(56) References Cited

U.S. PATENT DOCUMENTS

| | | | |
|---|---|---|---|
| 8,462,969 B2 | 6/2013 | Claussen | |
| 8,611,560 B2 | 12/2013 | Goldstein | |
| 8,873,779 B2 | 10/2014 | Lugger | |
| 9,307,332 B2* | 4/2016 | Rasmussen | H04R 25/43 |
| 9,576,593 B2 | 2/2017 | Pakhomov | |
| 10,856,087 B2* | 12/2020 | Pedersen | H04R 25/505 |
| 2007/0009122 A1 | 1/2007 | Hamacher | |
| 2014/0023213 A1 | 1/2014 | Zhang et al. | |
| 2014/0177868 A1 | 6/2014 | Jensen et al. | |
| 2014/0336448 A1 | 11/2014 | Banna | |
| 2015/0078600 A1* | 3/2015 | Rasmussen | H04R 25/407 381/322 |
| 2016/0192089 A1 | 6/2016 | Merks | |
| 2016/0241974 A1* | 8/2016 | Jensen | H04R 25/505 |
| 2017/0359659 A1 | 12/2017 | Von Brasch et al. | |
| 2019/0200143 A1* | 6/2019 | Jensen | H04R 25/505 |
| 2021/0337306 A1* | 10/2021 | Pedersen | H04R 1/406 |

FOREIGN PATENT DOCUMENTS

| | | |
|---|---|---|
| CN | 106062746 A | 10/2016 |
| EP | 2242289 B1 | 12/2016 |

OTHER PUBLICATIONS

International Search Report and Written Opinion received in international application No. PCT/IB2019/050164, dated May 14, 2019 (13 pages).

* cited by examiner

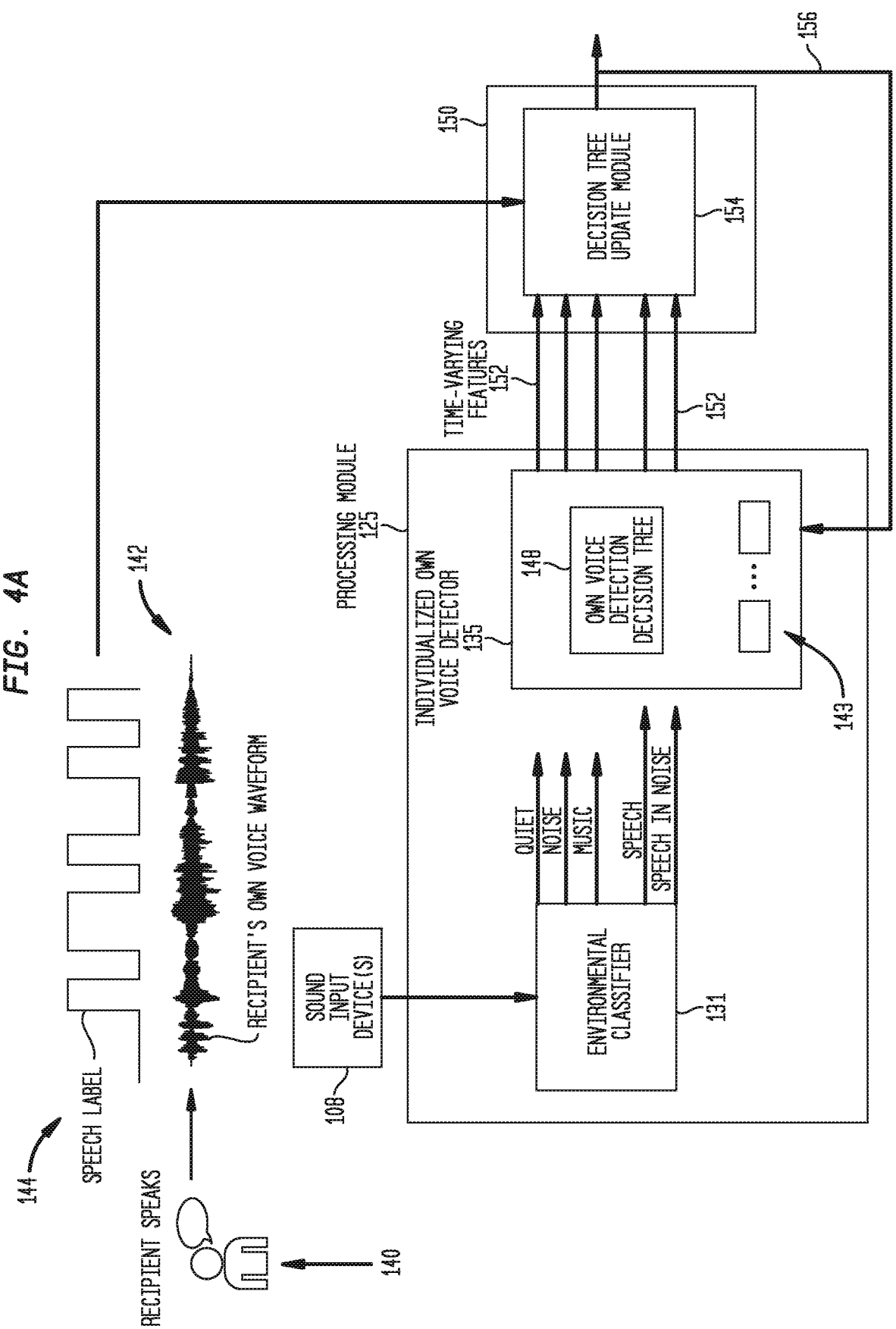

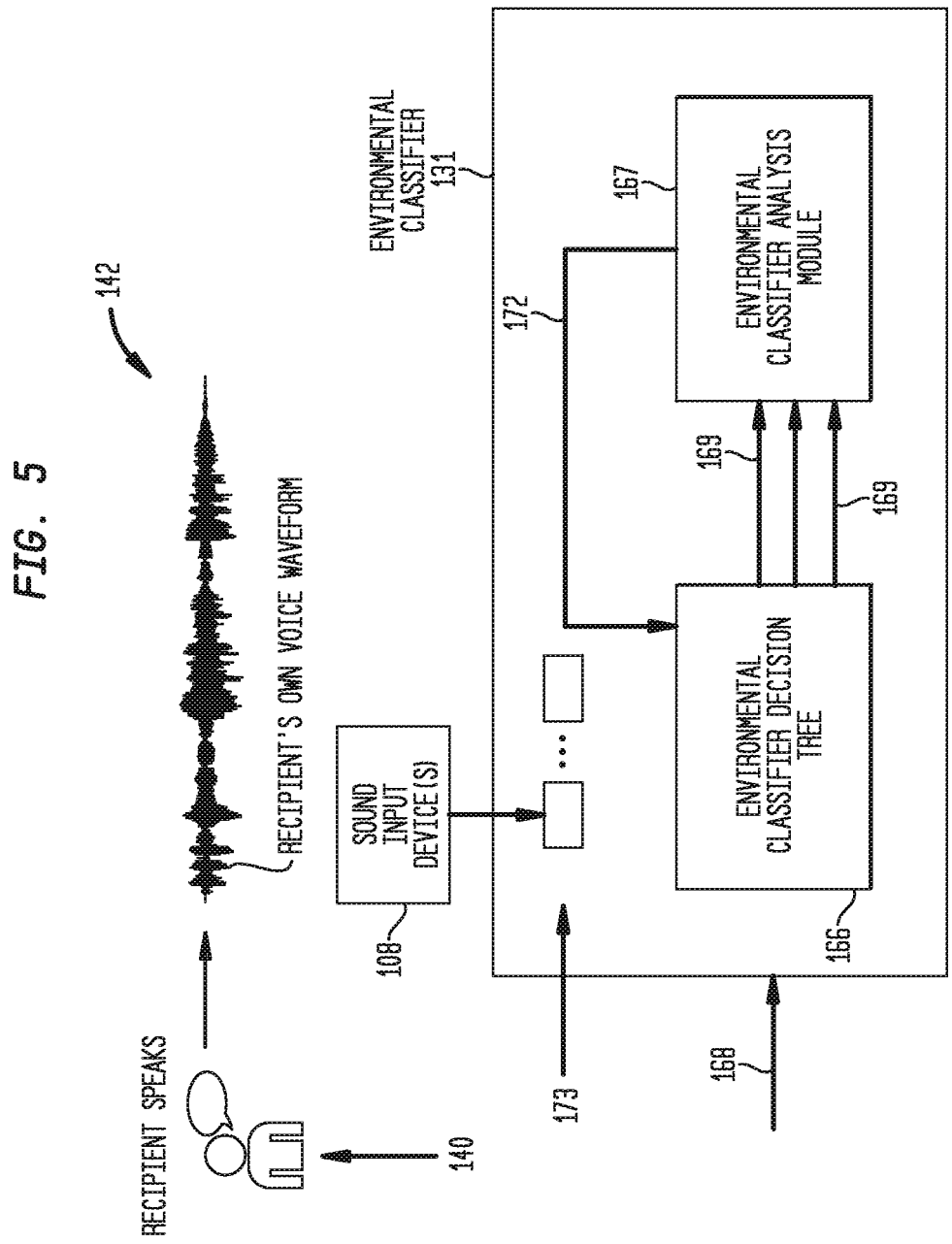

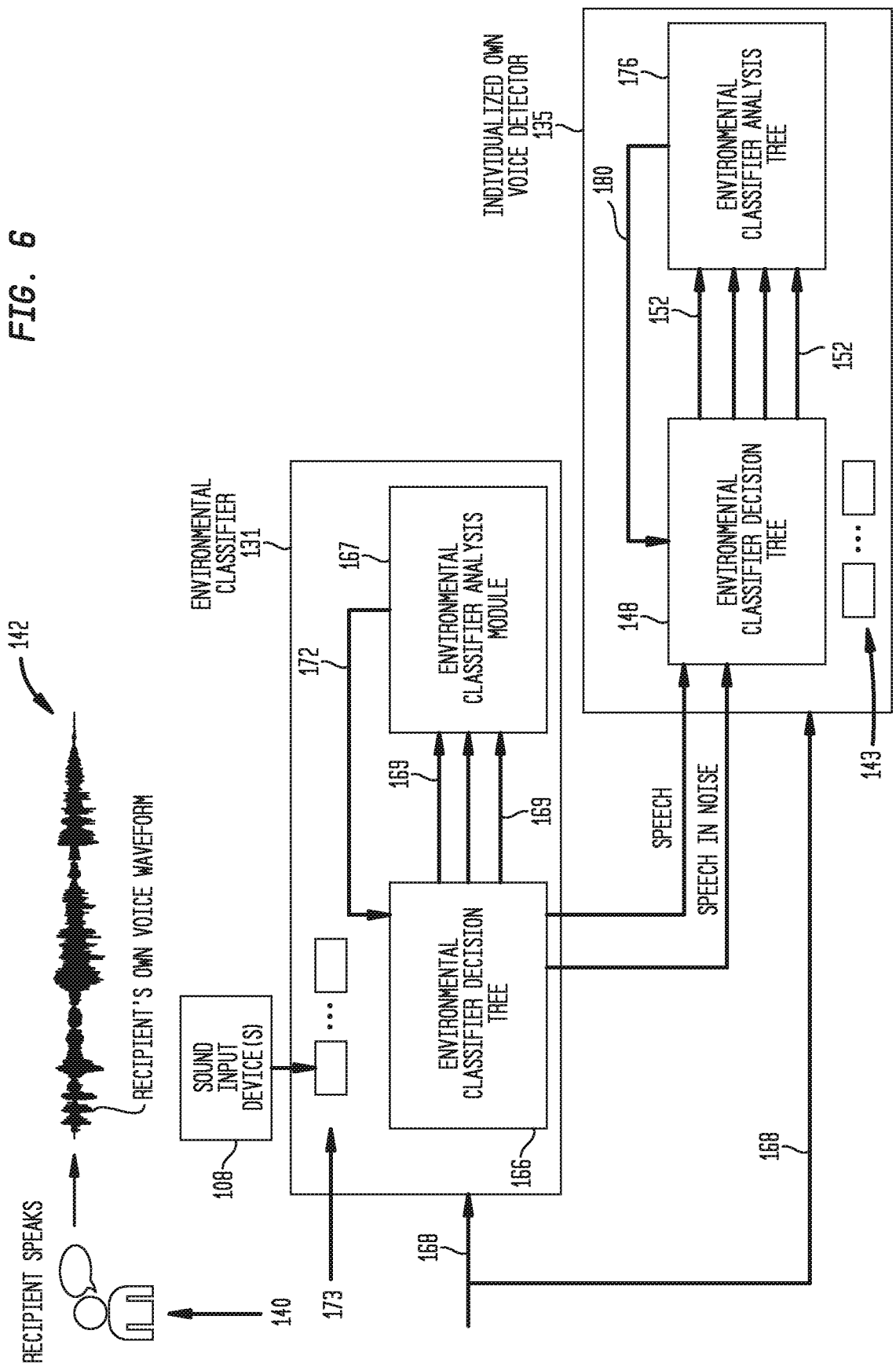

INDIVIDUALIZED OWN VOICE DETECTION IN A HEARING PROSTHESIS

BACKGROUND

Field of the Invention

The present invention generally relates to individualized own voice detection in hearing prosthesis.

Related Art

Hearing loss, which may be due to many different causes, is generally of two types, conductive and/or sensorineural. Conductive hearing loss occurs when the normal mechanical pathways of the outer and/or middle ear are impeded, for example, by damage to the ossicular chain or ear canal. Sensorineural hearing loss occurs when there is damage to the inner ear, or to the nerve pathways from the inner ear to the brain.

Individuals who suffer from conductive hearing loss typically have some form of residual hearing because the hair cells in the cochlea are undamaged. As such, individuals suffering from conductive hearing loss typically receive an auditory prosthesis that generates motion of the cochlea fluid. Such auditory prostheses include, for example, acoustic hearing aids, bone conduction devices, and direct acoustic stimulators.

In many people who are profoundly deaf, however, the reason for their deafness is sensorineural hearing loss. Those suffering from some forms of sensorineural hearing loss are unable to derive suitable benefit from auditory prostheses that generate mechanical motion of the cochlea fluid. Such individuals can benefit from implantable auditory prostheses that stimulate nerve cells of the recipient's auditory system in other ways (e.g., electrical, optical and the like). Cochlear implants are often proposed when the sensorineural hearing loss is due to the absence or destruction of the cochlea hair cells, which transduce acoustic signals into nerve impulses. An auditory brainstem stimulator is another type of stimulating auditory prosthesis that might also be proposed when a recipient experiences sensorineural hearing loss due to damage to the auditory nerve.

Certain individuals suffer from only partial sensorineural hearing loss and, as such, retain at least some residual hearing. These individuals may be candidates for electro-acoustic hearing prostheses.

SUMMARY

In one aspect, a method is provided. The method comprises: at one or more microphones of a hearing prosthesis, capturing input audio signals that include a voice of a recipient of the hearing prosthesis; calculating, on the hearing prosthesis, time-varying features from the input audio signals; and updating, based on an analysis of a plurality of the time-varying features, operation of an own voice detection decision tree of the hearing prosthesis.

In another aspect, a method is provided. The method comprises: receiving input audio signals at a hearing prosthesis, wherein the input audio signals include speech of a recipient of the hearing prosthesis; calculating, on the hearing prosthesis, time-varying features from the input audio signals; analyzing a plurality of the time-varying features with an own voice detection decision tree on the hearing prosthesis; receiving label data associated the input audio signals, wherein the label data indicates which time segments of the input audio signals include the voice of a recipient; analyzing the plurality of time-varying features and the label data to generate updated weights for the own voice detection decision tree; and updating the own voice detection decision tree with the updated weights.

In another aspect, a method is provided. The method comprises: receiving time-varying features generated from input audio signals captured at one or more microphones of a hearing prosthesis, wherein the input audio signals include a voice of a recipient of the hearing prosthesis; receiving label data associated the input audio signals, wherein the label data indicates which of the plurality of time segments of the input audio signals include the voice of a recipient; analyzing the plurality of time-varying features and the label data to generate updated weights for an own voice detection decision tree on the hearing prosthesis; and updating the own voice detection decision tree with the updated weights to generate an updated an own voice detection decision tree.

BRIEF DESCRIPTION OF THE DRAWINGS

Embodiments of the present invention are described herein in conjunction with the accompanying drawings, in which:

FIG. 4A is a schematic block diagram illustrating updating of an individualized own voice detection decision tree, in accordance with certain embodiments presented herein;

FIG. 5 is a schematic block diagram illustrating a technique for dynamically updating an environmental classification decision tree on a hearing prosthesis, in accordance with certain embodiments presented herein;

FIG. 6 is a schematic block diagram illustrating a technique for dynamically updating an environmental classification decision tree and an own voice detection tree on a hearing prosthesis, in accordance with certain embodiments presented herein;

DETAILED DESCRIPTION

Presented herein are techniques for training a hearing prosthesis to classify/categorize captured/received input audio signals as either including a recipient's own voice (i.e., the voice or speech of the recipient of the hearing prosthesis) external voice (i.e., the voice or speech of one or more persons other than the recipient). The techniques presented herein use the captured voice (speech) of the recipient to train the hearing prosthesis to perform the classification of the input audio signals as including the recipient's own voice or external voice.

There are a number of different types of hearing prostheses in which embodiments of the present invention may be implemented. However, merely for ease of illustration, the techniques presented herein are primarily described with reference to one type of hearing prosthesis, namely a cochlear implant. It is to be appreciated that the techniques presented herein may be used with, or implemented on/by, other hearing prostheses, such as auditory brainstem stimulators, hearing aids, electro-acoustic hearing prostheses, bimodal hearing prosthesis, bilateral hearing prosthesis, etc.

Figure 1A:
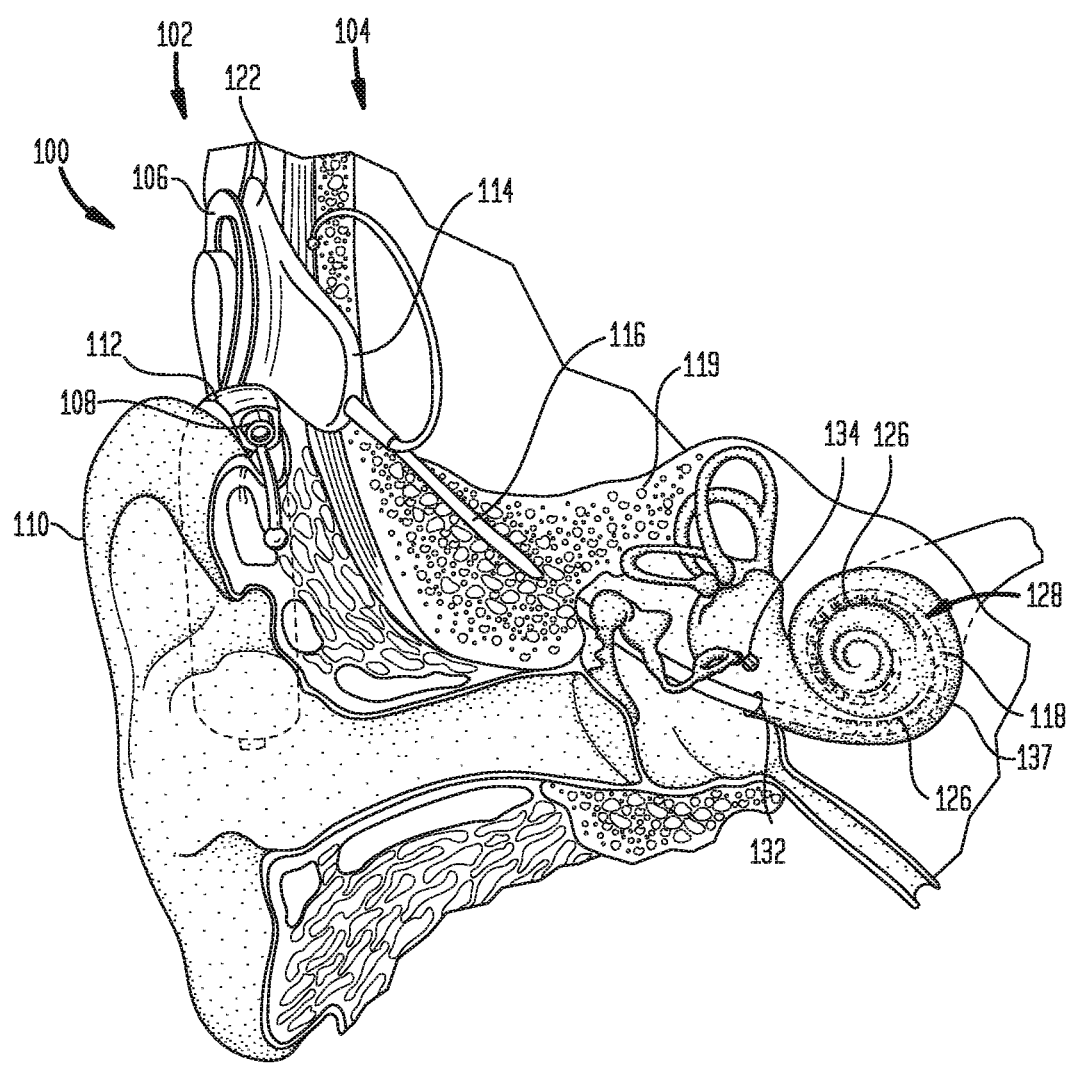
FIG. 1A is a schematic diagram illustrating a cochlear implant, in accordance with certain embodiments presented herein.
Figure 1B:
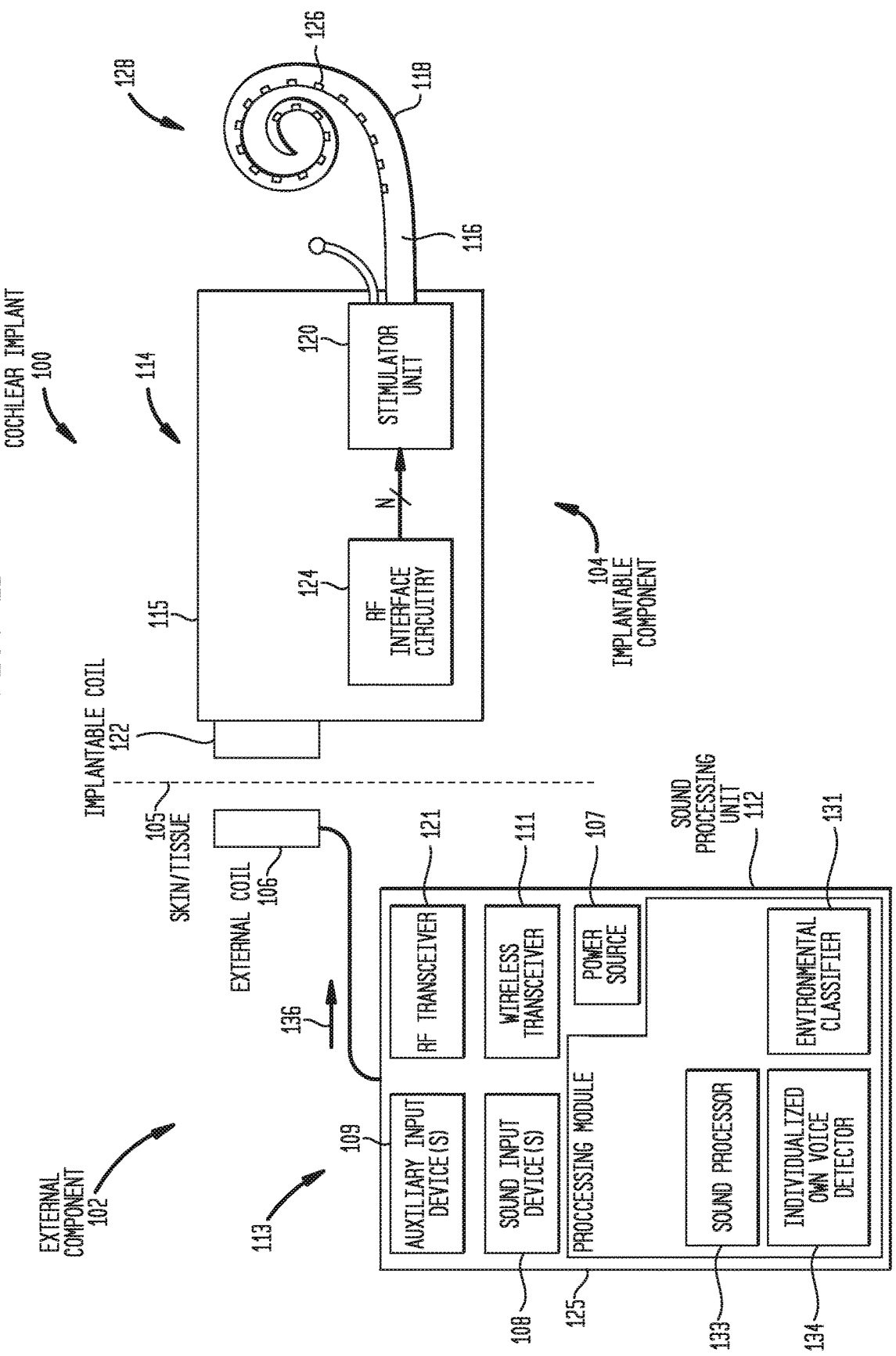
FIG. 1B is a block diagram of the cochlear implant of FIG. 1A.

FIG. 1A is a schematic diagram of an exemplary cochlear implant 100 configured to implement aspects of the techniques presented herein, while FIG. 1B is a block diagram of the cochlear implant 100. For ease of illustration, FIGS. 1A and 1B will be described together.

The cochlear implant 100 comprises an external component 102 and an internal/implantable component 104. The external component 102 is directly or indirectly attached to the body of the recipient and typically comprises an external coil 106 and, generally, a magnet (not shown in FIG. 1) fixed relative to the external coil 106. The external component 102 also comprises one or more input elements/devices 113 for receiving input signals at a sound processing unit 112. In this example, the one or more one or more input devices 113 include sound input devices 108 (e.g., microphones positioned by auricle 110 of the recipient, telecoils, etc.) configured to capture/receive input signals, one or more auxiliary input devices 109 (e.g., audio ports, such as a Direct Audio Input (DAI), data ports, such as a Universal Serial Bus (USB) port, cable port, etc.), and a wireless transmitter/receiver (transceiver) 111, each located in, on, or near the sound processing unit 112.

The sound processing unit 112 also includes, for example, at least one battery 107, a radio-frequency (RF) transceiver 121, and a processing module 125. The processing module 125 comprises a number of elements, including an environmental classifier 131, a sound processor 135, and an individualized own voice detector 135. Each of the environmental classifier 131, the sound processor 135, and the individualized own voice detector 135 may be formed by one or more processors e.g., one or more Digital Signal Processors (DSPs), one or more uC cores, etc.), firmware, software, etc. arranged to perform operations described herein. That is, the environmental classifier 131, the sound processor 135, and the individualized own voice detector 135 may each be implemented as firmware elements, partially or fully implemented with digital logic gates in one or more application-specific integrated circuits (ASICs), partially or fully in software, etc.

As described further below, the individualized own voice detector 135 includes a decision tree, sometimes referred to herein as an own voice detection decision tree, that can be trained/updated. Similarly, the environmental classifier 131 includes a decision tree, sometimes referred to as an environmental classifier decision tree that, in certain embodiments, can also be trained/updated. To provide the ability to train/update the own voice detection decision tree and/or the environmental classifier decision tree, the decision trees are stored in volatile memory and exposed to, for example, other process for updating thereof. As such, the environmental classifier 131 and the individualized own voice detector 135 are at least partially implemented in volatile memory.

In the examples of FIGS. 1A and 1B, the sound processing unit 112 is a behind-the-ear (BTE) sound processing unit configured to be attached to, and worn adjacent to, the recipient's ear. However, it is to be appreciated that embodiments of the present invention may be implemented by sound processing units having other arrangements, such as by a button sound processing unit (i.e., a component having a generally cylindrical shape and which is configured to be magnetically coupled to the recipient's head), etc., a mini or micro-BTE unit, an in-the-canal unit that is configured to be located in the recipient's ear canal, a body-worn sound processing unit, etc.

Returning to the example embodiment of FIGS. 1A and 1B, the implantable component 104 comprises an implant body (main module) 114, a lead region 116, and an intra-cochlear stimulating assembly 118, all configured to be implanted under the skin/tissue (tissue) 105 of the recipient. The implant body 114 generally comprises a hermetically-sealed housing 115 in which RF interface circuitry 124 and a stimulator unit 120 are disposed. The implant body 114 also includes an internal/implantable, coil 122 that is generally external to the housing 115, but which is connected to the RF interface circuitry 124 via a hermetic feedthrough (not shown in FIG. 1B).

As noted, stimulating assembly 118 is configured to be at least partially implanted in the recipient's cochlea 137. Stimulating assembly 118 includes a plurality of longitudinally spaced intra-cochlear electrical stimulating contacts (electrodes) 126 that collectively form a contact or electrode array 128 for delivery of electrical stimulation (current) to the recipient's cochlea. Stimulating assembly 118 extends through an opening in the recipient's cochlea (e.g., cochleostomy, the round window, etc.) and has a proximal end connected to stimulator unit 120 via lead region 116 and a hermetic feedthrough (not shown in FIG. 1B). Lead region 116 includes a plurality of conductors (wires) that electrically couple the electrodes 126 to the stimulator unit 120.

As noted, the cochlear implant 100 includes the external coil 106 and the implantable coil 122. The coils 106 and 122 are typically wire antenna coils each comprised of multiple turns of electrically insulated single-strand or multi-strand platinum or gold wire. Generally, a magnet is fixed relative to each of the external coil 106 and the implantable coil 122. The magnets fixed relative to the external coil 106 and the implantable coil 122 facilitate the operational alignment of the external coil with the implantable coil. This operational alignment of the coils 106 and 122 enables the external component 102 to transmit data, as well as possibly power, to the implantable component 104 via a closely-coupled wireless link formed between the external coil 106 with the implantable coil 122. In certain examples, the closely-coupled wireless link is a radio frequency (RF) link. However, various other types of energy transfer, such as infrared (IR), electromagnetic, capacitive and inductive transfer, may be used to transfer the power and/or data from an external component to an implantable component and, as such, FIG. 1B illustrates only one example arrangement.

As noted above, sound processing unit 112 includes the processing module 125. The processing module 125 is configured to convert input audio signals into stimulation control signals 136 for use in stimulating a first ear of a recipient (i.e., the processing module 125 is configured to perform sound processing on input audio signals received at the sound processing unit 112). Stated differently, the sound processor 133 (e.g., one or more processing elements implementing firmware, software, etc.) is configured to convert the captured input audio signals into stimulation control signals 136 that represent electrical stimulation for delivery to the recipient. The input audio signals that are processed and converted into stimulation control signals may be audio signals received via the sound input devices 108, signals received via the auxiliary input devices 109, and/or signals received via the wireless transceiver 111.

In the embodiment of FIG. 1B, the stimulation control signals 136 are provided to the RF transceiver 121, which transcutaneously transfers the stimulation control signals 136 (e.g., in an encoded manner) to the implantable component 104 via external coil 106 and implantable coil 122. That is, the stimulation control signals 136 are received at the RF interface circuitry 124 via implantable coil 122 and provided to the stimulator unit 120. The stimulator unit 120 is configured to utilize the stimulation control signals 136 to generate electrical stimulation signals (e.g., current signals) for delivery to the recipient's cochlea via one or more stimulating contacts 126. In this way, cochlear implant 100 electrically stimulates the recipient's auditory nerve cells, bypassing absent or defective hair cells that normally transduce acoustic vibrations into neural activity, in a manner that causes the recipient to perceive one or more components of the input audio signals.

As noted, in addition to the sound processor 133, the processing module 125 also includes the environmental classifier 131. As described further below, the environmental classifier 131 (e.g., one or more processing elements implementing firmware, software, etc.) is configured to determine an environmental classification of the sound environment (i.e., determines the "class" or "category" of the sound environment) associated with the input audio signals received at the cochlear implant 100. In addition, also as described further below, the processing module 125 comprises the individualized own voice detector 135 (e.g., one or more processing elements implementing firmware, software, etc.) that is configured to perform individualized own voice detection (OVD). As used herein, own voice detection (OVD) generally refers to a process in which speech signals received at a hearing prosthesis are classified as either including the speech of the recipient of the hearing prosthesis (referred to herein as the recipient's own voice or simply own voice) or speech generated by one or persons other than the recipient (referred to herein as external voice). Also as used herein, individualized own voice detection (or individualized OVD) refers to own voice detection that is recipient-specific, meaning the own voice detection is at least partly trained to perform the own voice detection using (based on) the specific voice (speech) of the recipient of the hearing prosthesis, as captured by the hearing prosthesis itself. As a result, the individualized own voice detection is specific/customized to the recipient of the hearing prosthesis and to the hearing prosthesis itself.

Figure 2:
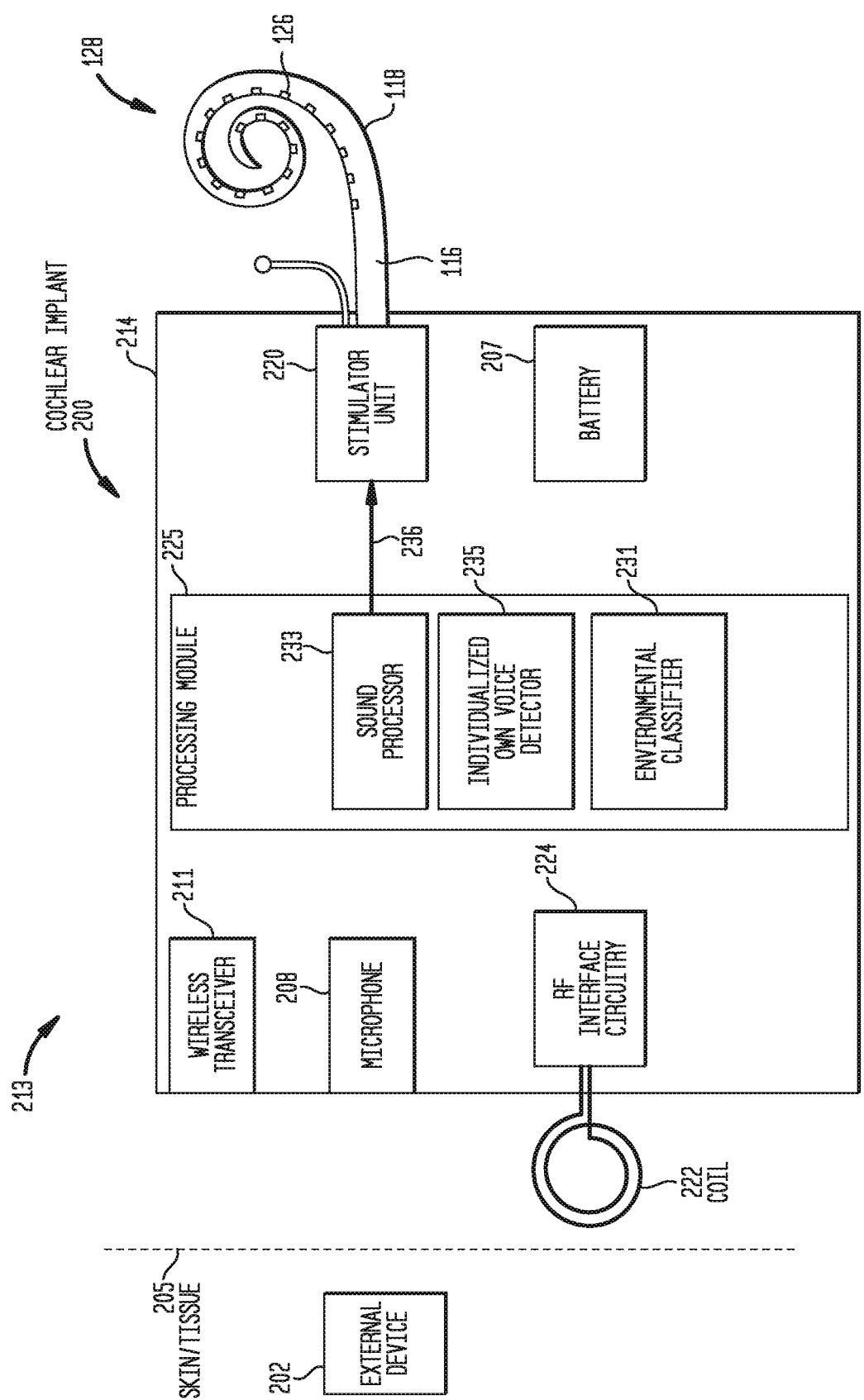
FIG. 2 is a block diagram of a totally implantable cochlear implant, in accordance with certain embodiments presented herein.

FIGS. 1A and 1B illustrate an arrangement in which the cochlear implant 100 includes an external component. However, it is to be appreciated that embodiments of the present invention may be implemented in cochlear implants having alternative arrangements. For example, FIG. 2 is a functional block diagram of an exemplary totally implantable cochlear implant 200 configured to implement embodiments of the present invention. Since the cochlear implant 200 is totally implantable, all components of cochlear implant 200 are configured to be implanted under skin/tissue 205 of a recipient. Because all components are implantable, cochlear implant 200 operates, for at least a finite period of time, without the need of an external device. An external device 202 can be used to, for example, charge an internal power source (battery) 207. External device 202 may be a dedicated charger or a conventional cochlear implant sound processor.

Cochlear implant 200 includes an implant body (main implantable component) 214, one or more input elements 213 for capturing/receiving input audio signals (e.g., one or more implantable microphones 208 and a wireless transceiver 211), an implantable coil 222, and an elongate intracochlear stimulating assembly 118 as described above with reference to FIGS. 1A and 1B. The microphone 208 and/or the implantable coil 222 may be positioned in, or electrically connected to, the implant body 214. The implant body 214 further comprises the battery 207, RF interface circuitry 224, a processing module 225, and a stimulator unit 220 (which is similar to stimulator unit 120 of FIGS. 1A and 1B). The processing module 225 may be similar to processing module 125 of FIGS. 1A and 1B, and includes environmental classifier 231, sound processor 233, and individualized own voice detector 235, which are similar to the environmental classifier 131, sound processor 133, the individualized own voice detector 135, respectively, described with reference to FIG. 1B.

In the embodiment of FIG. 2, the one or more implantable microphones 208 are configured to receive input audio signals. The processing module 225 is configured to convert received signals into stimulation control signals 236 for use in stimulating a first ear of a recipient. Stated differently, sound processor 233 is configured to convert the input audio signals into stimulation control signals 236 that represent electrical stimulation for delivery to the recipient.

As noted above, FIGS. 1A and 1B illustrate an embodiment in which the external component 102 includes the processing module 125. As such, in the illustrative arrangement of FIGS. 1A and 1B, the stimulation control signals 136 are provided to the implanted stimulator unit 120 via the RF link between the external coil 106 and the internal coil 122. However, in the embodiment of FIG. 2 the processing module 225 is implanted in the recipient. As such, in the embodiment of FIG. 2, the stimulation control signals 236 do not traverse the RF link, but instead are provided directly to the stimulator unit 220. The stimulator unit 220 is configured to utilize the stimulation control signals 236 to generate electrical stimulation signals that are delivered to the recipient's cochlea via one or more stimulation channels.

In addition to the sound processing operations, as described further below, the environmental classifier 231 is configured to determine an environmental classification of the sound environment associated with the input audio signals and the individualized own voice detector 235 is configured to perform individualized own voice detection (OVD).

As noted, the techniques presented herein may be implemented in a number of different types of hearing prostheses. However, for ease of description, further details of the techniques presented herein will generally be described with reference to cochlear implant 100 of FIGS. 1A-1B.

As noted above, own voice detection (OVD) generally refers to a process in which speech signals received at a hearing prosthesis are classified as either including, the "voice" or "speech" of the recipient of the hearing prosthesis (referred to herein as the recipient's own voice or simply "own voice") or the speech by one or persons other than the recipient (referred to herein as "external voice"). A classification of received speech signals as own voice or external voice may be helpful in, for example, providing information about how well the recipient performs with the hearing prosthesis (i.e., by indicating how much the recipient speaks and, accordingly, providing information of how "actively" the recipient uses the prosthesis), if a recipient speaks a large percentage of time, then the recipient is active and, accordingly, the recipient can understand other the speech of others (i.e., the recipient is hearing well) and the hearing prosthesis is operating as intended to improve the recipient's life. Own voice detection may enable the determination of a percentage of time a person's own voice is detected, a percentage of time an external voice is detected, and a percentage of time otherwise (e.g., in quiet or noise)

However, it is non-trivial task to distinguish between own voice and external voice and conventional own voice detection techniques attempt to do so with generic algorithms/processes. These generic algorithms/processes can be inaccurate and unreliable (e.g., when the recipient speaks, a generic own voice detection process may incorrectly decide that an external speaker is speaking). To address these problems, the techniques presented herein use a "recipient-specific" or "individualized" own voice detector that is trained/updated using the speech of the specific-recipient of the hearing prosthesis. That is, as described further below, the recipient's own voice is used to train, and potentially dynamically update, the individualized own voice detector. As a result, the individualized own voice detector is specific/customized to the recipient of the hearing prosthesis and to the hearing prosthesis. Since, own voice detection is tailored specifically to the speech of the recipient (and to the specific hearing prosthesis), the result is improved accuracy in classifying input audio signals as own voice or external voice. In turn, this improved classification accuracy enables more accurate data to be logged from the device, which is important so that clinicians have reliable data for prescription/therapy of the recipient. Incorrect data can lead to false evidence of a recipient's understanding of speech/conversations/ability to hear/engagement in life.

Figure 3:
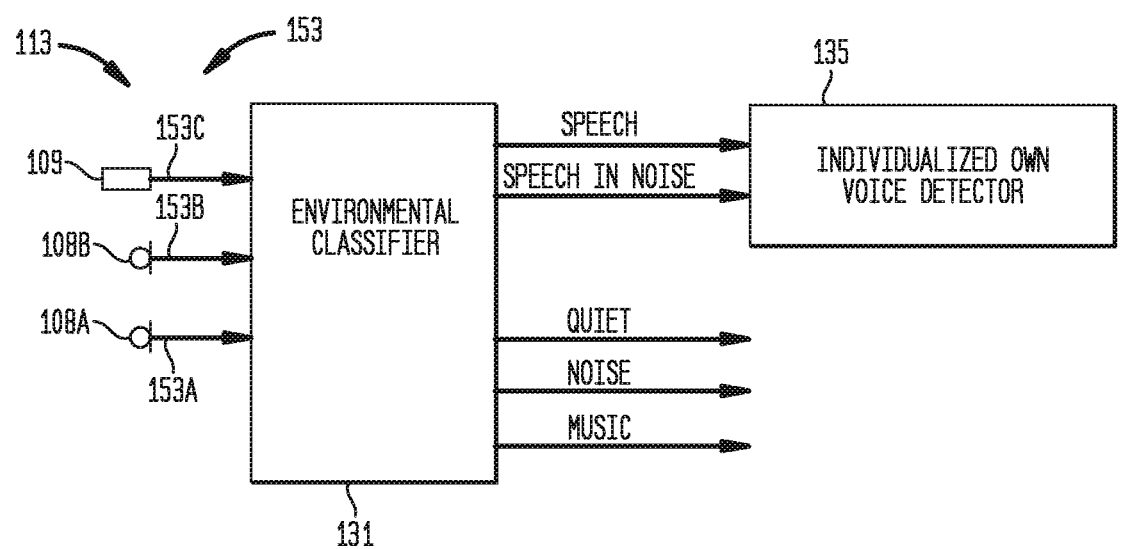
FIG. 3 is a schematic block diagram illustrating operation of an environmental classifier and individualized own voice detector, in accordance with certain embodiments presented herein.

Before describing training of an individualized own voice detector, the general operation of the individualized own voice detector is described with reference to FIG. 3. More specifically, FIG. 3 is a functional block diagram illustrating further details of the sound processing module 125 of cochlear implant 100, including the environmental classifier 131 and individualized own voice detector 135. For ease of illustration, elements that are not related to the environmental classification and own voice detection have been omitted from FIG. 3.

As noted, the cochlear implant 100 comprises one or more input devices 113. In the example of FIG. 3, the input elements 113 comprise a first microphone 108A, a second microphone 108B, and at least one auxiliary input 109 (e.g., an audio input port, a cable port, a telecoil, etc.). If not already in an electrical form, input devices 113 convert received/input audio signals into electrical signals 153, referred to herein as electrical input signals, which represent the input audio signals. As shown in FIG. 3, the electrical input signals 153 include electrical input signal 153A from microphone 108A, electrical input signal 153B from microphone 108B, and electrical input signal 153C from auxiliary input 115.

The electrical input signals 153 are provided to the environmental classifier 131. The environmental classifier 131 is configured to evaluate/analyze attributes of the input audio signals (represented by the electrical input signals 153) and, based on the analysis, determine a "class" or "category" of the sound environment associated with the input audio signals. The environmental classifier 131 may be configured to categorize the sound environment into a number of classes/categories. In one illustrative example, the environmental classifier 131 is configured to categorize the sound environment into one of five (5) categories, including "Speech," "Speech in Noise," "Quiet," "Noise," and "Music," although other categories are possible.

In certain embodiments, the environmental classifier 131 operates to determine a category for the set of input audio signals by calculating, in real-time, a plurality of time-varying features from the input audio signals and analyzing the calculated time-varying features using a using a type of decision structure tree. As a result of the analysis, the environmental classifier 131 determines the most likely category for the set of input audio signals. Stated differently, the environmental classifier 131 includes a number of processes/algorithms that calculate time-varying features from the input audio signals. The environmental classifier 131 also includes a decision tree that uses all or some of these time-varying features as inputs. The decision tree includes a number of hierarchical/linked branches/nodes that each perform evaluations/comparisons/checks using at least one of the time-varying features to determine the classification at the branch ends (leaves).

As noted above, own voice detection is a process in which speech signals received at a hearing prosthesis, such as cochlear implant 100, are classified as either including the voice/speech of the recipient or speech generated by one or more persons other than the recipient. As such, own voice detection is only relevant for the categories of the input audio signals, as determined by the environmental classifier 131, that include speech, namely the "Speech" and "Speech in Noise" categories (sometimes collectively referred to herein as speech classes or categories). Stated differently, as shown in FIG. 3, when the environmental classifier 131 determines the input audio signals are associated with a speech class (e.g., "Speech" or "Speech in Noise"), then the input audio signals are further classified by the individualized own voice detector 135 as either being own voice (i.e., the hearing prosthesis recipient is speaking within the set of input audio signals) or as external voice (i.e., someone other than the hearing prosthesis recipient is speaking within the set of input audio signals The individualized own voice detector 135 operates by calculating, in real-time, a plurality of time-varying features from the input audio signals (as represented by the electrical input signals 153) and analyzing the calculated time-varying features using a using a type of decision tree. As a result of the analysis, the individualized own voice detector 135 determines the most likely category (i.e., either own voice or external voice) for the set of input audio signals. Stated differently, the individualized own voice detector 135 includes a number of processes/algorithms that calculate time-varying features from the input audio signals. The individualized own voice detector 135 also includes a decision tree that uses all or some of these time-varying features as inputs. The decision tree includes a number of hierarchical/linked branches/nodes that each perform evaluations/comparisons/checks using at least one of the time-varying features to determine the classification (i.e., own or external voice) at the branch ends (leaves). That is, the decision tree traverses its "branches" until it arrives at a "leaf" and decides "own" or "external."

In accordance with embodiments presented herein, the individualized own voice detector 135 can calculate a number of different time-varying features from the input audio signals and the specific features may vary for different implementations. For example, the own voice detector 135 may calculate time-varying features such as amplitude modulations, spectral profile, harmonicity, amplitude onsets, etc.

In general, the decision tree of the own voice detector 135 checks the values of different time-varying features and the combination of the values of the various time-varying features, relative to pre-determined conditions (weights), determine the result. For example, in one illustrative arrangement, the own voice detector 135 may utilize five (5) time-varying features and three (3) of these features need to have values of 0.5 or greater, and 2 of these need to have values of 0.7 or greater, in order to generate a determination of own voice, otherwise the resulting determination is external voice.

In order to create a decision tree that is accurate, the decision tree needs appropriate weighting for evaluation of each relevant time-varying feature (i.e., the evaluation condition(s) for the nodes need to be set correctly). To create these weightings (evaluation condition or conditions of a node), in accordance with embodiments presented herein, the decision tree is initially trained in advance using the voice (speech) of the recipient of the hearing prosthesis in a machine learning process. As a result, the weightings used in the nodes of the own voice decision tree in accordance with embodiments presented herein are specifically individualized/personalized for the specific recipient.

As noted, the environmental classifier 131 and the individualized own voice detector 135 each make use of decision trees. For ease of illustration and description, the environmental classifier 131 and the individualized own voice detector 135, as well as the corresponding decision trees, are described as separate functional entities. However, it is to be appreciated that the environmental classifier 131 and the individualized own voice detector 135 may be implemented as a single element using two decision trees or decision tree segments that operate in a parent/child relationship to generate the different classifications (i.e., the environmental classification and the own voice classification).

FIG. 4A is a schematic diagram illustrating training of an individualized own voice detector in accordance with embodiments presented herein. For ease of illustration, FIG. 4A will be described with reference to the cochlear implant 100 of FIGS. 1A, 1B, and 3.

FIG. 4A illustrates a clinical setting in which the cochlear implant 100 is in communication (e.g., wired or wireless communication) with a computing device 150, such as a fitting system. In this example, the recipient, generally represented in FIG. 4A at 140, of the cochlear implant 100 is instructed to speak. The recipient's speech may be elicited in a number of different manners. For example, the recipient 140 may be instructed to provide free-form speech, to describe a picture or other item, to read one or more sentences, paragraphs, etc. In certain examples, the recipient's speech is elicited so as to include questions, statements, singing, and normal conversations.

The recipient's speech results in the generation of a "recipient own voice waveform," which is generally represented in FIG. 4A at 142. While the recipient 140 is speaking (i.e., during generation of the recipient own voice waveform 142), the recipient, clinician, or other user provides a user input at the cochlear implant 100, computing device 150, or another device to generate a "speech label" 144. In one example, the speech label 144 is created by the recipient, clinician, or other user by pressing and holding a button while the recipient 140 is actually speaking and releasing the button while the recipient 140 is not speaking. The result is a time-varying (e.g., square-wave) speech label 144 that is generated in real-time and provided to the computing device 150. As described further below, the time-varying label 144 that is time synchronized with the speech of the recipient.

In FIG. 4A, the recipient own voice waveform 142 (i.e., the recipient's speech) is also captured/received by one or more sound input devices 108 of the cochlear implant 100, along with any other ambient sounds in the clinical environment. The input audio signals, including the recipient own voice waveform 142, are provided (in electrical form) to the environmental classifier 131. The environmental classifier 131 operates to classify the input audio signals, for given time periods, within one of the predetermined categories (e.g., "Speech," "Speech in Noise," "Noise," "Quiet," "Music," etc.).

If the environmental classifier 131 determines that the input audio signals are associated with a speech class (e.g., are classified as "Speech" or "Speech in Noise" signals), then the input audio signals are provided to the individualized own voice detector 135. The individualized own voice detector 135 includes a plurality of feature calculators 143 (i.e., processes/algorithms) that, for a given time period, calculate a plurality of different time-varying features from the input audio signals. The time-varying features vary over time, but are not necessarily linearly with the input (e.g., if the audio signal is very loud, then very soft, one time-varying feature may not change at all, while another time-varying feature may change rapidly). In general, each time-varying feature is the output of a specifically engineered feature-calculation algorithm that operates blind and independent of the other feature-calculation algorithm and comprise the data used by the decision tree to determine whether or not the input audio signals include own voice. These time-varying features may include, for example, volume level, proximity level, modulation depth, etc.

In certain embodiments, the time-varying features are continuously generated and the outputs of the feature calculators 143 are sampled at discrete intervals (e.g., every 100 values, every 10 milliseconds, etc.) and these samples are subsequently used, as described below, by the environmental classifier 131 and/or in a training process.

The environmental classifier 131 includes an own voice detection decision tree 148 that uses the time-varying features (as calculated by the plurality of feature calculators 143 and sampled at the outputs thereof) to classify the input audio signals within a predetermined time period/segment as either Own Voice or External Voice. The time segments may have different lengths (e.g., 100 milliseconds, a second, several seconds, etc.) in different embodiments.

It is to be appreciated that, at the beginning of a clinical fitting process, the individualized own voice detector 135 has not yet been "individualized" or "personalized" for the recipient. Instead, the own voice detection decision tree 148 is initially programmed as a generic (i.e., not individualized) decision tree that operates to make the initial own voice or external voice classification at the outset of a fitting process based on (using) standard (non-recipient specific) voice samples. The initial programming of the own voice detection decision tree 148 using standard voice samples is simply to provide a baseline for operation of the decision tree upon receipt of the input audio signals within the clinic. Therefore, at the beginning of a clinical fitting process, the own voice detection decision tree 148 can be referred to as a "generic" or "standard" own voice detection. However, as described below, as the training process continues, the own voice detection decision tree 148 becomes personalized to the recipient and the hearing prosthesis.

Returning to the example of FIG. 4A, as noted above, for each of the analyzed time periods/segments, the individualized own voice detector 135 (i.e., the own voice detection decision tree 148) generates a classification of the signals within the associated period as being either own voice or external voice. After the individualized own voice detector 135 generates one or more these classifications, the individualized own voice detector 135 sends the calculated time-varying features, generated by the feature calculators 143, to the computing device 135. In FIG. 4A, the calculated time-varying features are generally represented by arrows 152.

In the arrangement of FIG. 4A, the computing device 150 includes a decision tree update module 154. The decision tree update module 154 is configured to execute machine learning, using the time-varying features 152 received from the cochlear implant 100 and the speech label 144, to train/update the own voice detection decision tree. Stated differently, the computing device 150 performs machine learning to generate, in real-time, updated own voice decision tree weights 156 (i.e., updates to the conditions for evaluation of a time varying feature at nodes of the own voice detection decision tree 148). Further details of the machine learning process at the decision tree update module 154 are described further below.

As shown in FIG. 4A, the updated decision tree weights 156 (i.e., updated evaluation conditions) are then provided back to the individualized own voice detector 135. The individualized own voice detector 135 then updates the current implementation of the own voice detection decision tree 148 with the updated weights 156 received from the computing device 150 (i.e., the updated decision tree weights are sent back to the processing module and the running decision tree is updated in real time the received weights). In general, updating weights of the updated decision tree include, for example, setting a hierarchy of checks for time-varying features in or across nodes and/or setting values for features to trigger different decisions at one or more nodes.

The process shown in FIG. 4A may be repeated a number of times, where the same or different recipient speech is analyzed with each iteration. In general, with each iteration, the own voice decision tree 148 is further customized for the recipient.

Figure 4B:
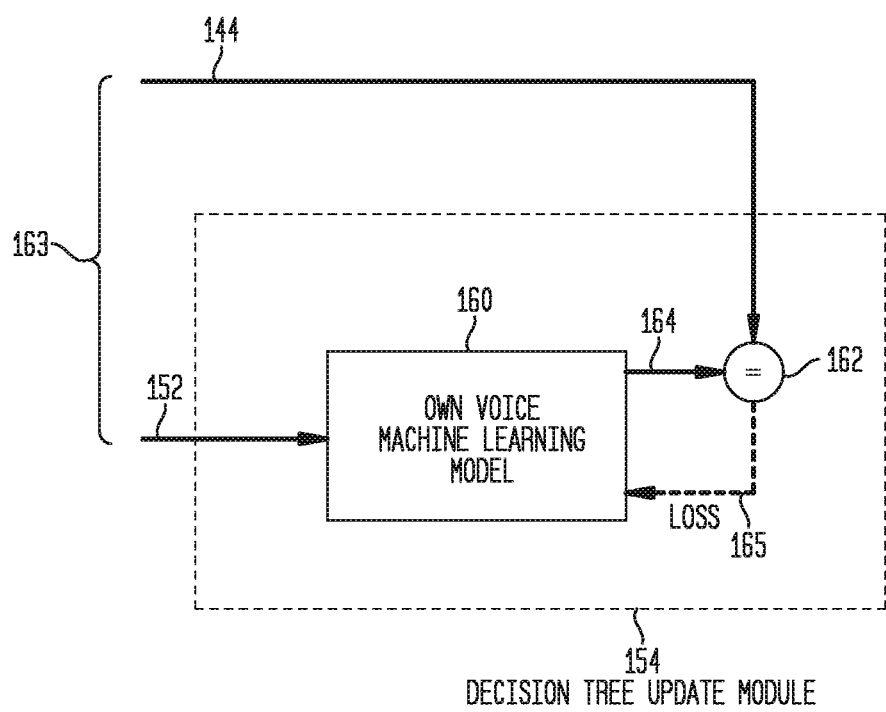
FIG. 4B is a schematic block diagram illustrating further details of one implementation of the arrangement of FIG. 4A.

As noted above, the decision tree update module 154 is configured to execute machine learning, using the time-varying features 152 received from the cochlear implant 100 and the speech label 144, to train/update the own voice detection decision tree weights. FIG. 4B is a schematic diagram illustrating further details of one example implementation of the decision tree update module 154. It is to be appreciated that the machine learning at decision tree update module 154 may be implemented in a number of different manners and, as such, the implementation of FIG. 4B is merely illustrative.

As shown in FIG. 4B, the decision tree update module 154 includes own voice decision tree 160 and a loss function 162. As noted above, the decision tree update module 154 receives the time-varying features 152 generated by the own voice detection tree 148, as well as the time-varying speech label 144. The time-varying features 152 and the speech label 144 are time synchronized (i.e, linked/associated) so as to form, for a given time period, a data-label pair 163. That is, a data-label pair 163 is comprised of the time-varying features 152 determined for a time period (i.e., the data) and the time-varying speech label 144 (i.e., the label) for the same corresponding time period. As noted, the time-varying features 152 are features calculated from the input audio signals and analyzed by the own voice detection decision tree 148 and, as such, generally illustrate the "classification" of the input audio signals made by the own voice detection decision tree 148 for the corresponding time period. The speech label 144 is the authoritative (actual) classification of the input audio signals at the same time period generated, for example, by the recipient, clinician, or other user button push.

In the example of FIG. 4B, the own voice decision tree 160 uses the time-varying features 152 received from the cochlear implant 100 to generate a predicted classification 164 for a given time period. The loss function 162 then calculates a "loss" using the predicted classification 164 and the speech label 144 associated with the same time period. The generated loss represents the error/difference between the predicted classification 164 generated by the own voice machine learning model 160 (i.e., using the data in the data-label pair) and the associated speech label 144 (the label in a data-label pair). The determined loss 165 is then fed back to the own voice decision tree 160 and used to adapt the decision tree weights until the predicted classification 164 matches the speech label 144 (i.e., the system trains itself by minimizing the loss/error).

Eventually, after updating using one or more data-label pairs 163, the weights of the own voice decision tree 160 (i.e., the updated decision tree weights 156 of FIG. 4A) are sent to the cochlear implant 100 for instantiation as the own voice detection decision tree 148 (i.e., replacement of the previous instance of the own voice detection decision tree 148). At this time instance, the own voice detection decision tree 148 generally matches the own voice decision tree 160 that has been updated at the computing device 150. However, through subsequent machine learning training, the own voice decision tree 160 will eventually evolve and begin to operate differently from the own voice detection decision tree 148, at least until the own voice detection decision tree 148 is updated/replaced using further updated weights received from the computing device 150.

FIGS. 4A and 4B have generally been described with reference to one implementation in which speech of the recipient is captured, labeled, and used to update the own voice detection decision tree 148. However, it is to be appreciated that the processes of FIG. 4A and/or FIG. 4B can be executed with other types of inputs. For example, in one alternative arrangement, external speech (e.g., speech of the clinician or a caregiver) may be captured, labeled (as described above) and used to update the own voice detection decision tree 148. In such examples, a data-label pair received at the decision tree update module 154 will still include the time-varying parameters 152, but the label will indicate external voice at the corresponding time period, rather than indicate own voice as in the arrangement of FIGS. 4A and 4B. In still other examples, the recipient or external speech may be captured with or without the presence of background noise to train the own voice detection decision tree 148 to operate in different environments. In other examples, the own voice detection decision tree 148 may be updated using previously recorded "external speech," "own speech in noise" and "external noisy speech in noise" (i.e., recorded audio samples) to at least initialize the decision tree.

In summary, FIGS. 4A and 4B generally illustrate arrangements in which the individualized own voice detector 135 and, more specifically, the own voice detection decision tree 148 is trained using the recipient's own voice/speech. FIGS. 4A and 4B illustrate a supervised learning approach, where labeled input data is used to train the algorithm(s). Through the training of FIGS. 4A and 4B, the own voice detection decision tree 148 (i.e., the decision tree weights) is specifically customized to the characteristics of the recipient's voice (speech).

In addition, it should be noted that the cochlear implant 100 includes a number of electrical components (e.g., microphones, processors, etc.) that have associated operating characteristics/properties that be different from the electrical components on other devices. In the embodiments of FIGS. 4A and 4B, these electrical components, and thus the associated operating characteristics, are implicitly used in the training process, e.g., through the receiving of the input audio signals, generating the environmental and own voice classifications, etc. As a result, the training process described above will inherently account for the electrical properties of the individual sound processors, thus improving the accuracy of the decision tree relative to generic own voice detection by removing electrical idiosyncrasies from the real-time operational analysis.

After initial training of the individualized own voice detector 135, such as that described with reference to FIGS. 4A and 4B, the recipient is sent home and the individualized own voice detector 135 operates to classify input audio signals as either own voice or external voice. However, in accordance with further embodiments presented herein, operation of the own voice detection decision tree 148 may also be updated outside of a clinical setting. FIG. 5 is a schematic diagram illustrating one example arrangement for updating operation of the own voice detection decision tree 148 by dynamically updating operation of the environmental classifier 131.

More specifically FIG. 5 illustrates that the environmental classifier 131 includes an environmental classifier decision tree 166 and an environmental classifier analysis module 167. In this example, the recipient speaks and the speech is captured by the sound input device(s) 108. While the recipient is speaking, the recipient or other user provides a user input (e.g., deliberately presses a button) to override operation of the environmental classifier decision tree 166. This button press, which is generally represented in FIG. 5 by arrow 168, indicates that the signals received during that time period (i.e., while the button is pressed) should be classified as speech (e.g., either "Speech" or "Speech in Noise" signals). That is, the input audio signals received during the time period are labeled by the user as speech and, as such, the environmental classifier 131 has the opportunity to update the environmental classifier decision tree 166 based on the content of the input audio signals.

When the user overrides operation of the environmental classifier decision tree 166, the time-varying feature analyzed by the environmental classifier decision tree 166, during the override time period, are provided to the environmental classifier analysis module 167. Similar to the above examples, these time-varying features, which are represented in FIG. 5 by arrow 169, are calculated by feature extractors 173 (e.g., processes/algorithms) which operate on the input audio signals. The values of the time-varying features analyzed by the environmental classifier decision tree 166 during the override time period are sometimes referred to herein as "manual" feature values because they are the values of the time-varying feature when the user manually sets the classification to a speech class (e.g., "Speech" or "Speech in Noise"). The environmental classifier analysis module 167 operates by analyzing the values of the time-varying features during the override time period, and the resulting classification by the decision tree 166 (i.e., ether own or external voice) in view of the so-called "automated" time-varying feature values and automated decision tree operation. That is, a comparison is done on the existing feature checks by the environmental classifier decision tree 166 (i.e., referred to as the automated feature values) and the manual feature checks. Because the user has manually set the environmental classifier decision tree to a speech class, the system determines that all incoming signals are going to be speech. As such, the analysis module 167 checks to determine whether the time-varying feature values that are provided by the environmental classifier decision tree 166 in this override (manual) period are different to those in the existing checks done by the decision tree (i.e., automated). If they are significantly different by some threshold or other definable metric (e.g., by more than 50% of the original setting), then the operation of the environmental classifier decision tree 166 can be adjusted. Adjustment of the environmental classifier decision tree 166 is generally represented in FIG. 5 by arrow 172.

FIG. 5 illustrates an arrangement in with operation of the environmental classifier decision tree 166, rather than the own voice detection decision tree 148 (FIG. 4A), is adjusted. However, the example of FIG. 5 improves the performance of the own voice detection decision tree 148 because the certainty of speech is higher when the input audio signals are received at the individualized own voice detector 135. In a further embodiment, the own voice detection decision tree 148 may also be updated along with the environmental classifier tree 166. Such an arrangement is illustrated in FIG. 6

More specifically, FIG. 6 first illustrates the environmental classifier 131 implemented as described above with reference to FIG. 5. As described above with reference to FIG. 5, the environmental classifier decision tree 166 can be adjusted, on the cochlear implant 100, in response to a user input (e.g., button press) 168.

However, FIG. 6 also illustrates the individualized own voice detector 135, which in this example includes the own voice detection decision tree 148 and an own voice detector analysis module 176. As noted above with reference to FIG. 5, the recipient speaks and the speech is captured by the sound input device(s) 108. While the recipient is speaking, the recipient or other user provides a user input 168 (e.g., deliberately presses a button). In the example of FIG. 6, this user input 168 overrides both the environmental classifier decision tree 166 and the own voice detection decision tree 148.

As noted above, this user input 168 indicates that the signals received during that time period (i.e., while the button is pressed) are speech signals. However, in the specific arrangement of FIG. 6, the user input 168 also indicates that the signals are own voice, meaning that the indicated speech is the recipient's own speech. As a result, the individualized own voice detector 135 has the opportunity to update the own voice detection decision tree 148 based on the content of the input audio signals.

When the user overrides operation of the own voice detection decision tree 148 (via user input 168), the calculated time-varying features, represented in FIG. 6 by arrow 152, are provided to the own voice detector analysis module 176. The feature values of the own voice detection decision tree 148 during the override time period are sometimes referred to herein as "manual" feature values because they are the feature values when the user manually sets the classification to a class that includes own voice. The own voice detector analysis module 176 operates by comparing the "manual" feature values to so-called "automated" feature values of the own voice detection decision tree 148. That is, a comparison is done on the existing feature checks by the own voice detection decision tree 148 (i.e., referred to as the automated feature values) and the manual feature values (i.e., feature values calculated override (manual) time period). Because the user has manually set the own voice detection decision tree 148 to the own voice class, the system determines that all incoming signals are going to be own voice. As such, the analysis module 176 checks to determine whether the feature values that are provided by the own voice detection decision tree 148 in this override (manual) period are different to those in the existing checks done by the decision tree (i.e., automated). If they are significantly different by some threshold or definable metric (e.g., by more than 50% of the original setting) then the operation of the own voice detection decision tree 148 can be adjusted. Adjustment of the own voice detection decision tree 148 is generally represented in FIG. 5 by arrow 180.

Figure 7:
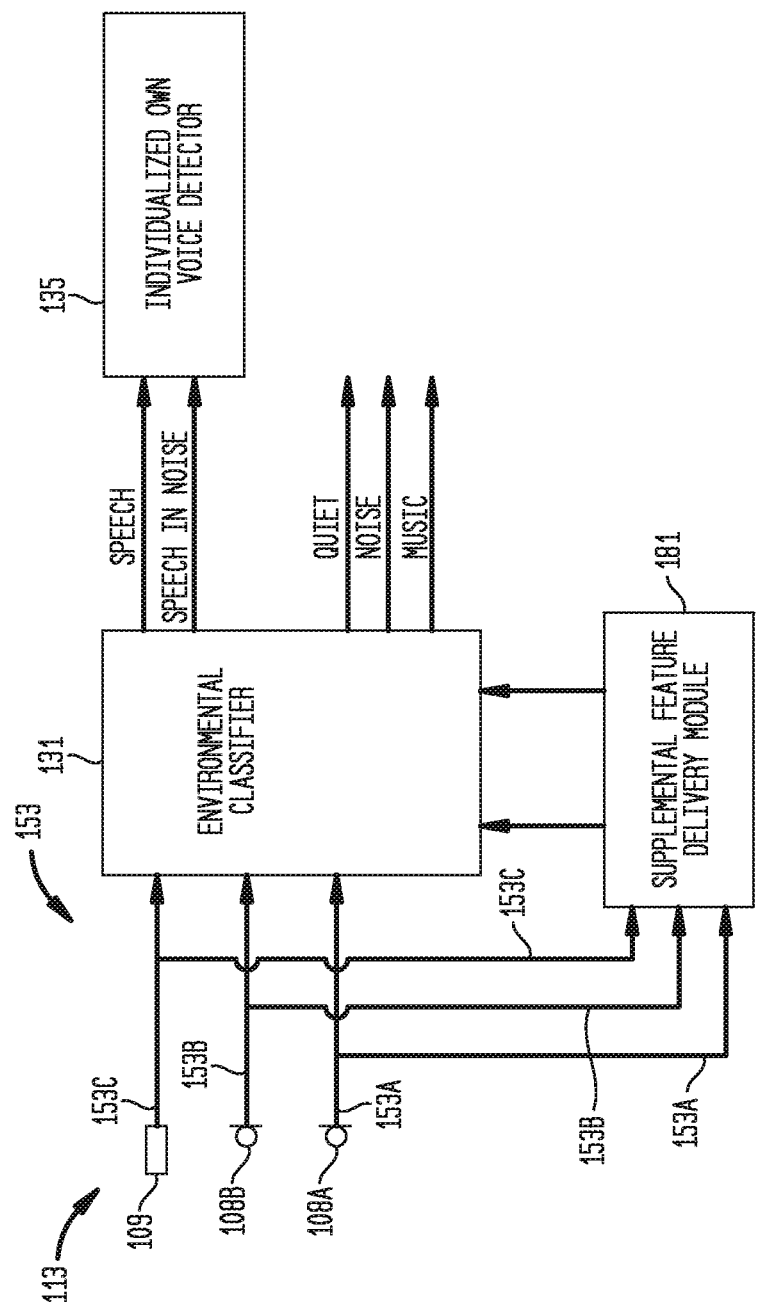
FIG. 7 is a schematic block diagram illustrating use of supplemental signal features in an environmental classification, in accordance with certain embodiments presented herein.

As noted, FIG. 5 generally illustrates an embodiment in which operation of the environmental classifier 131 is dynamically updated based on a user input. FIG. 7 illustrates another embodiment in which the operation of the environmental classifier 131 is dynamically updated based on one or more time-varying features calculated from input audio signals.

More specifically, some value calculated on the device has a relationship with the input signal(s) that can be used in the environmental classifier. In the example of FIG. 7, a supplemental feature delivery module 181 is provided. The supplemental feature delivery 181 is configured to receive the input audio signals (represented by the electrical input signals 153 described above) and is configured implement a process to calculated and deliver time-varying features (e.g., fundamental frequency (F0), an estimate of a harmonic signal power-to-total power ratio (STR), etc.) to the environmental classifier 131 to provide further information regarding the probability of the signal being "Speech,". As such, in these examples, the classification of a current sound environment associated with input audio signals is based, at least in part, on one or more supplemental time-varying features, such estimate of a harmonic signal power-to-total power ratio (SIR) associated with the input audio signals, an estimate of a fundamental frequency (F0) associated with the input audio signals, etc. In certain arrangements, these time-varying features can be included one or more of the above embodiments to improve the decision tree at mapping time in clinic, or dynamically post clinic. The example of FIG. 7 improves the performance of the own voice detection decision tree 148 because the certainty of speech is higher when the input audio signals are received at the individualized own voice detector 135.

Figure 8:
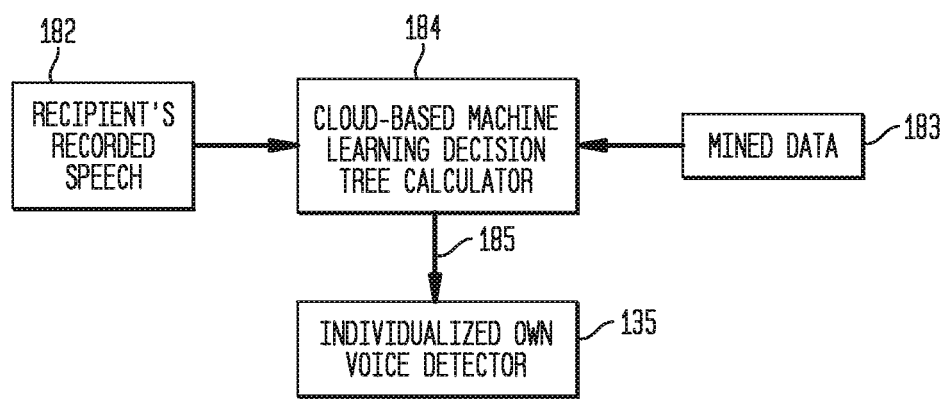
FIG. 8 is a block diagram illustrating a cloud-based arrangement for dynamically updating an own voice detection tree, in accordance with certain embodiments presented herein.

FIG. 8 is a schematic diagram illustrating that, in certain embodiments, the individualized own voice detector 135 can be dynamically updated using a remote or cloud-based arrangement. For example, the recipient's speech 182 may be recorded (e.g., during a fitting session, off-line, etc.) and stored, for example, in the cloud and, post-clinic, the individualized own voice detector 135 can be trained further using this recorded speech. For example, if new data 183 has been mined which improves "external speech" detection, a cloud-based machine learning decision tree calculator 184 may take the existing/recorded speech 182 (e.g., from the recipient's clinical session) and combine it with the new external speech data 183 to generate a new own voice detection decision tree 185. This new own voice detection decision tree 185 may be provided to, and instantiated at, the individualized own voice detector 135. In this example, the cloud-based machine learning decision tree calculator 184 can be Internet-based, or can be implemented on a local server with a local database.

Figure 9:
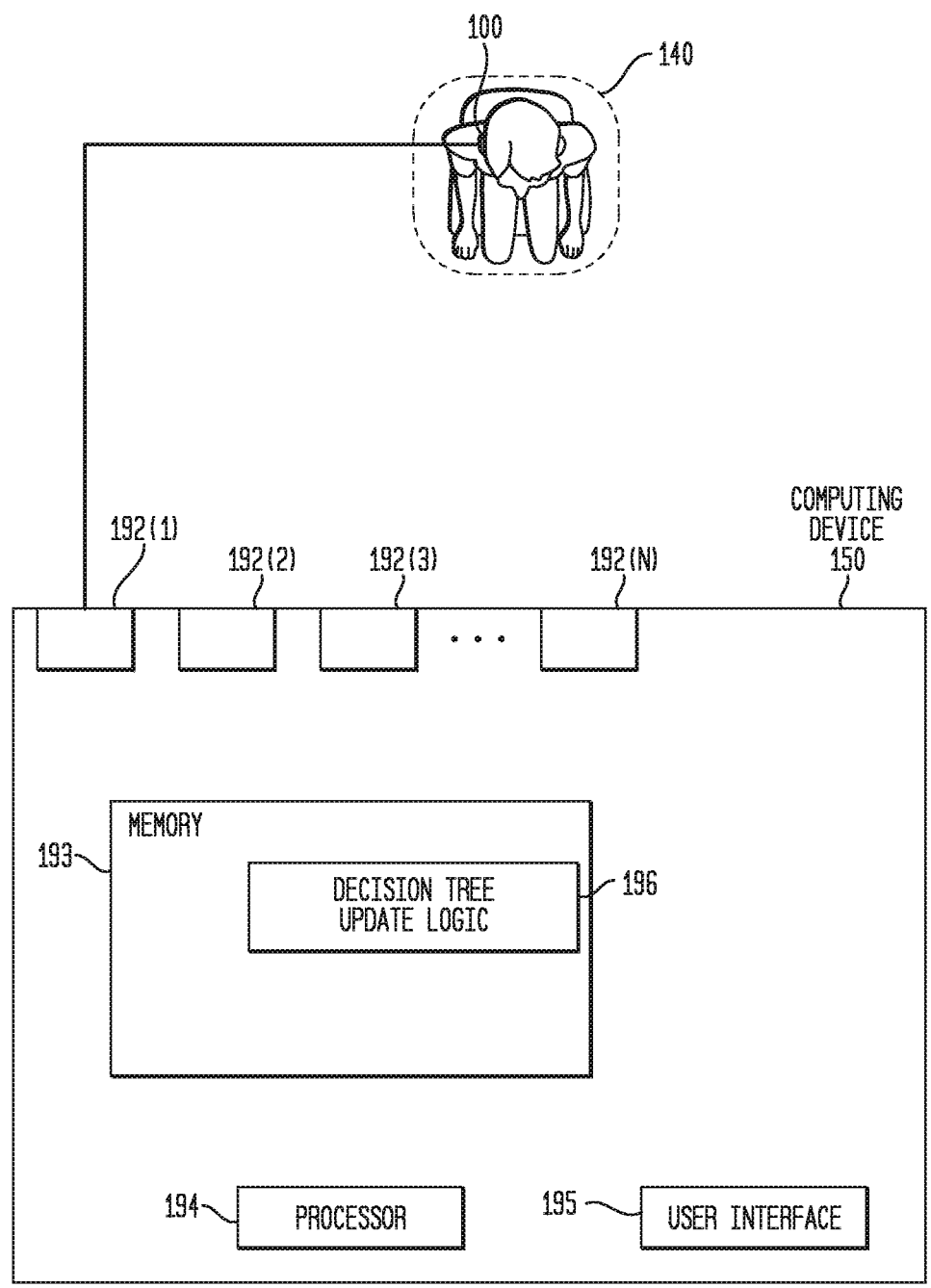
FIG. 9 is a block diagram of a fitting system for implementation of certain techniques presented herein.

As noted above, in accordance with embodiments presented herein, an own voice detection decision tree and/or an environmental classification decision tree may be dynamically updated on/by a hearing prosthesis itself, such as cochlear implant 100, or updated using an external computing device, such as external computing device 150 described above with reference to FIGS. 4A and 4B. FIG. 9 is a block diagram illustrating one example arrangement for external computing device 150 configured to perform one or more operations in accordance with certain embodiments presented herein.

External computing device 150 comprises a plurality of interfaces/ports 192(1)-192(N), a memory 193, a processor 194, and a user interface 195. The interfaces 192(1)-192(N) may comprise, for example, any combination of network ports (e.g., Ethernet ports), wireless network interfaces, Universal Serial Bus (USB) ports, institute of Electrical and Electronics Engineers (IEEE) 1394 interfaces, PS/2 ports, etc. In the example of FIG. 9, interface 192(1) is connected to cochlear implant 100 having components implanted in a recipient 140. Interface 192(1) may be directly connected to the cochlear implant 100 or connected to an external device that is communication with the cochlear implant 100. Interface 192(1) may be configured to communicate with the cochlear implant 100 via a wired or wireless connection.

The user interface 195 includes one or more output devices, such as a liquid crystal display (LCD) and a speaker, for presentation of visual or audible information to a clinician, audiologist, or other user. The user interface 195 may also comprise one or more input devices that include, for example, a keypad, keyboard, mouse, touchscreen, etc. that can accept a user input.

The memory 193 comprises decision tree update 196 that may be executed to generate or update an own voice detection decision tree (i.e., generate updated decision tree weights), as described elsewhere herein. It would be appreciated that memory 193 may include other logic elements that, for ease of illustration, have been omitted from FIG. 9.

Memory 193 may comprise read only memory (ROM), random access memory (RAM), magnetic disk storage media devices, optical storage media devices, flash memory devices, electrical, optical, or other physical/tangible memory storage devices. The processor 194 is, for example, a microprocessor or microcontroller that executes instructions for the apical protection logic 196. Thus, in general, the memory 193 may comprise one or more tangible (non-transitory) computer readable storage media (e.g., a memory device) encoded with software comprising computer executable instructions and when the software is executed (by the processor 194) it is operable to perform operations described herein.

It is to be appreciated that the arrangement for external computing device 150 shown in FIG. 9 is illustrative and that an external computing device 150 in accordance with embodiments presented herein may include any combination of hardware, software, and firmware configured to perform the functions described herein. For example, the external computing device 150 may be a personal computer, handheld device (e.g., a tablet computer), a mobile device (e.g., a mobile phone), and/or any other electronic device having the capabilities to perform the associated operations described elsewhere herein.

Figure 10:
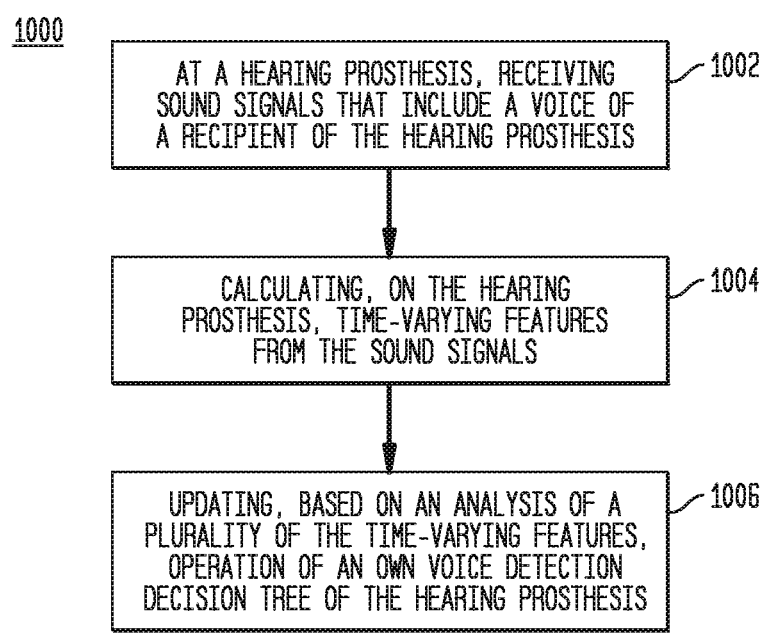
FIG. 10 is a flowchart of method, in accordance with embodiments presented herein.

FIG. 10 is a flowchart of method 1000, in accordance with embodiments presented herein. Method 1000 begins at 1002 where one or more microphones of a hearing prosthesis capture input audio signals that include a voice of a recipient of the hearing prosthesis. At 1004, the hearing prosthesis calculates time-varying features from the input audio signals. At 1006, based on an analysis of a plurality of the time-varying features, the operation of an own voice detection decision tree of the hearing prosthesis is updated.

Figure 11:
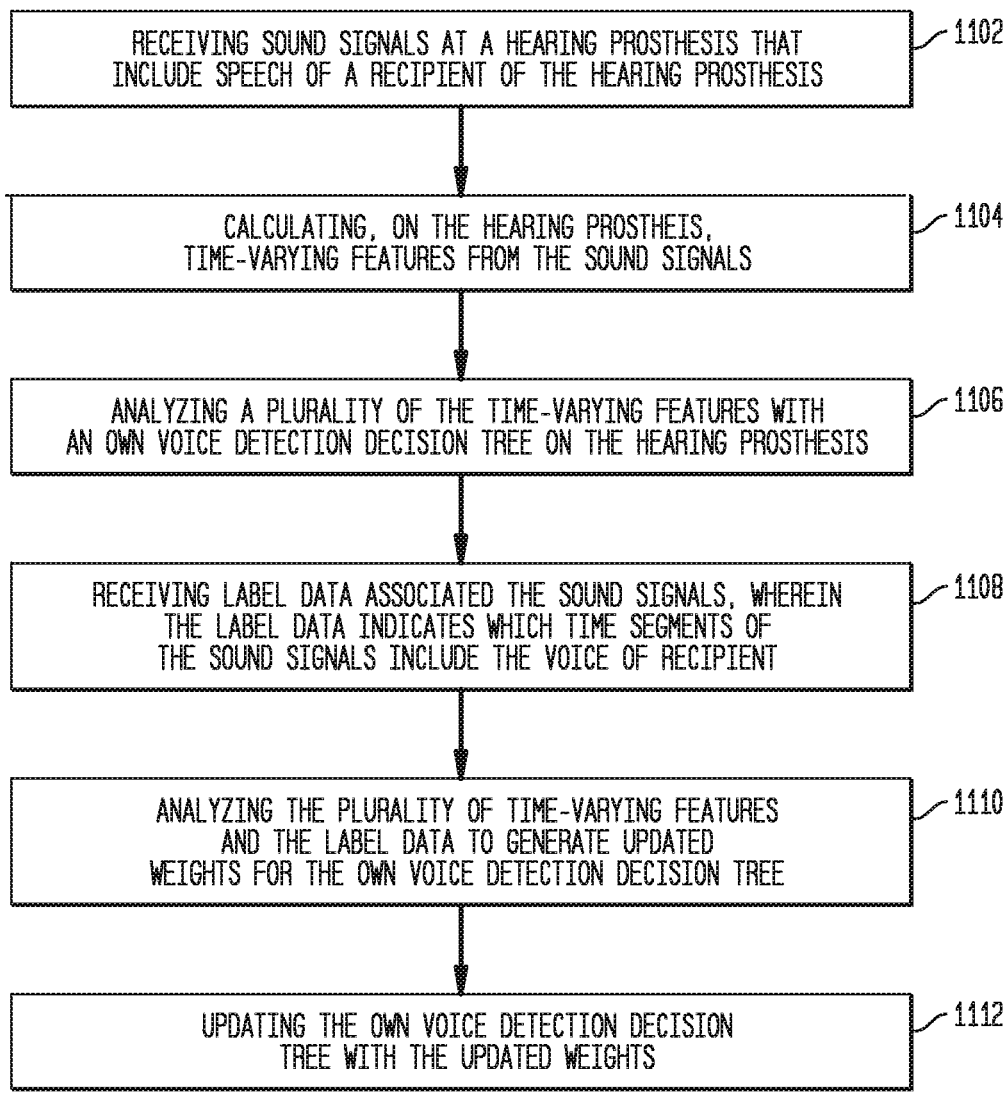
FIG. 11 is a flowchart of another method, in accordance with embodiments presented herein.

FIG. 11 is a flowchart of another method 1100, in accordance with embodiments presented herein. Method 1100 begins at 1102 where a hearing prosthesis receives input audio signals that include speech of a recipient of the hearing prosthesis. At 1104, the hearing prosthesis calculates time-varying features from the input audio signals. At 1106, a plurality of the time-varying features are analyzed with an own voice detection decision tree on the hearing prosthesis. At 1108, label data associated the input audio signals is received, where the label data indicates which time segments of the input audio signals include the voice of a recipient. At 1110, the plurality of time-varying features and the label data are analyzed to generate updated weights for the own voice detection decision tree. At 1112, the own voice detection decision tree is updated with the updated weights.

Figure 12:
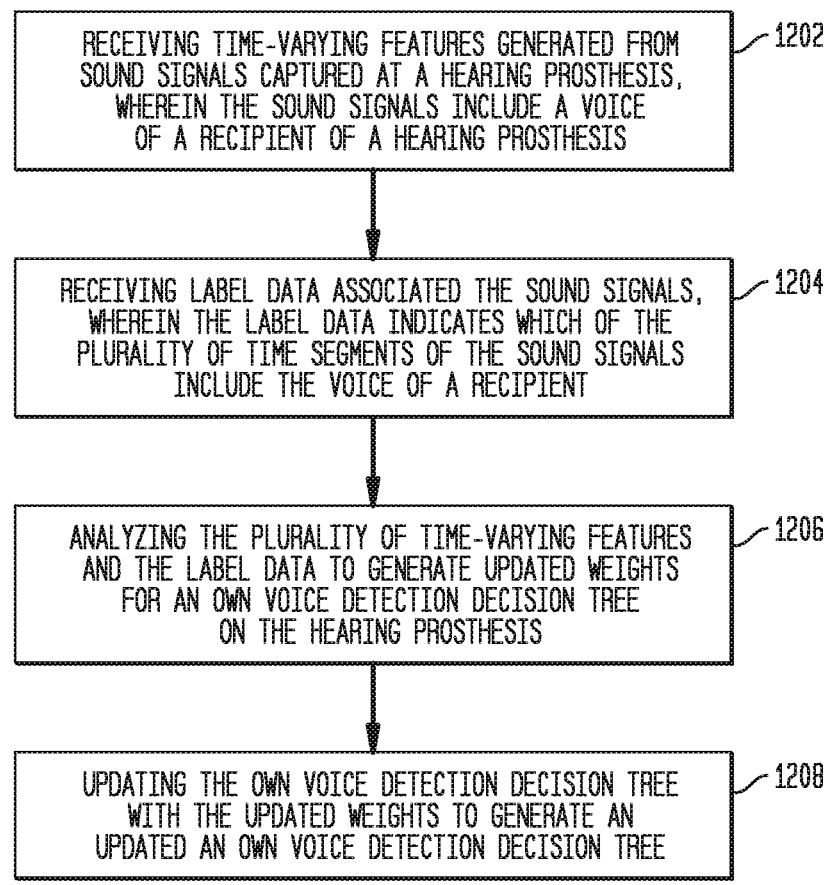
FIG. 12 is a flowchart of another method, in accordance with embodiments presented herein.

FIG. 12 is a flowchart of another method 1200, in accordance with embodiments presented herein. Method 1200 begins at 1202 where time-varying features generated from input audio signals captured at one or more microphones of a hearing prosthesis are received. The input audio signals include a voice of a recipient of a hearing prosthesis. At 1204, label data associated the input audio signals is received, wherein the label data indicates which of the plurality of time segments of the input audio signals include the voice of a recipient. At 1206, the plurality of time-varying features and the label data are analyzed to generate updated weights for an own voice detection decision tree on the hearing prosthesis. At 1208, the own voice detection decision tree is updated with the updated weights to generate an updated an own voice detection decision tree.

It is to be appreciated that the above described embodiments are not mutually exclusive and that the various embodiments can be combined in various manners and arrangements.

The invention described and claimed herein is not to be limited in scope by the specific preferred embodiments herein disclosed, since these embodiments are intended as illustrations, and not limitations, of several aspects of the invention. Any equivalent embodiments are intended to be within the scope of this invention. Indeed, various modifications of the invention in addition to those shown and described herein will become apparent to those skilled in the art from the foregoing description. Such modifications are also intended to fall within the scope of the appended claims.

What is claimed is:

1. A method, comprising:
    at one or more microphones of a hearing device, capturing input audio signals that include a voice of a recipient of the hearing device;
    determining, from the input audio signals, a primary classification of a current sound environment associated with the input audio signals, wherein the primary classification indicates that the current sound environment includes speech signals;
    after determining the primary classification, calculating, on the hearing device, time-varying features from the input audio signals; and
    updating, based on an analysis of a plurality of the time-varying features, operation of an own voice detection decision tree of the hearing device.

2. The method of claim 1, wherein the own voice detection decision tree is configured for classification of one or more time segments of input audio signals captured by the one or more microphones of the hearing device as either including the voice of the recipient or as including an external voice.

3. The method of claim 1, wherein updating, based on an analysis of the plurality of the time-varying features, operation of an own voice detection decision tree, comprises:
    obtaining a time-varying label that is time synchronized with the plurality of the time-varying features calculated on the hearing device; and
    analyzing the plurality of the time-varying features and the time-varying label to generate updated decision tree weights for the own voice detection decision tree.

4. The method of claim 3, wherein analyzing the plurality of the time-varying features and the time-varying label to generate updated decision tree weights for the own voice detection decision tree comprises:
    executing a machine learning process to analyze the plurality of the time-varying features representative of the recipient's voice relative to values of the time-varying label at corresponding times.

5. The method of claim 3, wherein the updated decision tree weights are generated at a computing device in communication with the hearing device, and wherein the method further comprises:
    receiving the updated decision tree weights at the hearing device; and
    instantiating the updated decision tree weights in the own voice detection decision tree of the hearing device.

6. The method of claim 5, further comprising:
    analyzing one or more input audio signals captured by the one or more microphones of the hearing device with the decision tree including the instantiated updated decision tree weights to classify time segments of the one or more input audio signals captured at the hearing device as either including the voice of the recipient or as including an external voice.

7. The method of claim 3, wherein analyzing the plurality of the time-varying features and the time-varying label comprises:
    analyzing the plurality of the time-varying features and the time-varying label on the hearing device; and
    adjusting the decision tree weights based on the analysis of the plurality of the time-varying features and the time-varying label on the hearing device.

8. The method of claim 3, wherein obtaining a time-varying label that is time synchronized with the plurality of the time-varying features comprises:
    receiving a user input indicating which time segments of the input audio signals captured by the one or more microphones of the hearing device include the voice of the recipient.

9. The method of claim 8, wherein receiving a user input comprises:
    receiving an input from the recipient of the hearing device.

10. The method of claim 8, wherein receiving a user input comprises:
receiving an input from an individual other than the recipient of the hearing device.

11. The method of claim 1, wherein determining the primary classification of a current sound environment associated with the input audio signals, comprises:
determining the primary classification of the current sound environment based in part on an estimate of a harmonic signal power-to-total power ratio (STR) associated with the input audio signals.

12. The method of claim 1, wherein determining the primary classification of a current sound environment associated with the input audio signals, comprises:
determining the primary classification of the current sound environment based in part on an estimate of a fundamental frequency (F0) associated with the input audio signals.

13. A method, comprising:
receiving input audio signals at a device, wherein the input audio signals include speech of a recipient of the device;
calculating, on the device, time-varying features from the input audio signals;
analyzing a plurality of the time-varying features with an own voice detection decision tree on the device;
receiving label data associated the input audio signals, wherein the label data indicates which time segments of the input audio signals include the voice of the recipient;
analyzing the plurality of the time-varying features and the label data to generate updated weights for the own voice detection decision tree; and
updating the own voice detection decision tree with the updated weights.

14. The method of claim 13, wherein the own voice detection decision tree is configured for classification of one or more time segments of input audio signals received at the device as either including the voice of the recipient or as including an external voice.

15. The method of claim 13, wherein the label data is time-varying and time synchronized with the plurality of the time-varying features.

16. The method of claim 13, wherein analyzing the plurality of the time-varying features and the label data to generate updated weights for the own voice detection decision tree comprises:
executing a machine learning process to generate the updated weights for the own voice detection decision tree based on the plurality of the time-varying features and the label data.

17. The method of claim 13, wherein the updated decision tree weights are generated at a computing device in communication with the device, and wherein updating the own voice detection decision tree with the updated weights comprises:
receiving the updated decision tree weights at the device; and
instantiating the updated decision tree weights in the own voice detection decision tree of the device.

18. The method of claim 13, further comprising:
analyzing one or more input audio signals received at the device with the own voice detection decision tree that has been updated with the updated weights to classify time segments of the input audio signals received at the device as either including the voice of the recipient or as including an external voice.

19. The method of claim 13, wherein analyzing the plurality of the time-varying features and the label data to generate updated weights for the own voice detection decision tree comprises:
analyzing the plurality of the time-varying features and the label data on the device to generate the updated weights.

20. The method of claim 13, wherein receiving label data associated the input audio signals comprises:
receiving a user input indicating which time segments of the input audio signals received at the device include the voice of the recipient.

21. The method of claim 20, wherein receiving a user input comprises:
receiving an input from the recipient of the device.

22. The method of claim 20, wherein receiving a user input comprises:
receiving an input from an individual other than the recipient of the device.

23. The method of claim 13, wherein prior to analyzing a plurality of the time-varying features with an own voice detection decision tree on the device, the method comprises:
determining on the device, from the input audio signals, a primary classification of a current sound environment associated with the input audio signals, wherein the primary classification indicates that the current sound environment includes speech signals.

24. The method of claim 23, wherein determining the primary classification of a current sound environment associated with the input audio signals, comprises:
determining the primary classification of the current sound environment based in part on an estimate of a harmonic signal power-to-total power ratio (STR) associated with the input audio signals.

25. The method of claim 23, wherein determining the primary classification of a current sound environment associated with the input audio signals, comprises:
determining the primary classification of the current sound environment based in part on an estimate of a fundamental frequency (F0) associated with the input audio signals.

26. A method, comprising:
receiving a plurality of time-varying features generated from input audio signals captured at one or more microphones of a device, wherein the input audio signals include a voice of a recipient of the device;
receiving label data associated the input audio signals, wherein the label data indicates which of a plurality of time segments of the input audio signals include the voice of the recipient;
analyzing the plurality of time-varying features and the label data to generate updated weights for an own voice detection decision tree on the device; and
updating the own voice detection decision tree with the updated weights to generate an updated an own voice detection decision tree.

27. The method of claim 26, wherein the own voice detection decision tree is configured for classification of one or more time segments of input audio signals received at the device as either including the voice of the recipient or as including an external voice.

28. The method of claim 26, wherein the label data is time-varying and time synchronized with the plurality of time-varying features.

29. The method of claim 26, wherein analyzing the plurality of time-varying features and the label data to generate updated weights for an own voice detection decision tree on the device comprises:
  executing a machine learning process to generate the updated weights for the own voice detection decision tree based on the plurality of time-varying features and the label data.

30. The method of claim 26, wherein the updated decision tree weights are generated at a computing device in communication with the device, and wherein updating the own voice detection decision tree with the updated weights comprises:
  sending the updated decision tree weights to the device.

31. The method of claim 26, wherein analyzing the plurality of time-varying features and the label data to generate updated weights for an own voice detection decision tree on the device comprises:
  analyzing the plurality of time-varying features and the label data on the device to generate the updated weights.

32. The method of claim 26, wherein receiving label data associated the input audio signals comprises:
  receiving a user input indicating which time segments of the input audio signals received at the device include the voice of the recipient.

\* \* \* \* \*